United States Patent [19]
Engel et al.

[11] Patent Number: 6,022,860
[45] Date of Patent: Feb. 8, 2000

[54] IMMOBILIZED AND ACTIVITY-STABILIZED COMPLEXES OF LHRH ANTAGONISTS AND PROCESSES FOR THEIR PREPARATION

[75] Inventors: Jürgen Engel, Alzenau; Wolfgang Deger; Thomas Reissmann, both of Frankfurt; Günter Losse, Dresden; Wolfgang Naumann, Zug; Sandra Murgas, Dresden, all of Germany

[73] Assignee: Asta Medica Aktiengesellschaft, Dresden, Germany

[21] Appl. No.: 09/048,244

[22] Filed: Mar. 26, 1998

[30] Foreign Application Priority Data

Mar. 26, 1997 [DE] Germany ............................ 197 12 718

[51] Int. Cl.⁷ .......................... A61K 38/00; A61K 38/09
[52] U.S. Cl. ................ 514/15; 514/12; 514/841; 514/951; 530/328; 530/331; 424/198.1
[58] Field of Search ................ 514/12, 15, 951, 514/841; 530/328, 313; 424/198.1

[56] References Cited

U.S. PATENT DOCUMENTS

| | | | |
|---|---|---|---|
| 4,341,767 | 7/1982 | Nestor et al. | 424/177 |
| 5,502,035 | 3/1996 | Haviv et al. | 514/15 |
| 5,700,459 | 12/1997 | Krone et al. | 424/78.08 |
| 5,773,032 | 6/1998 | Engel et al. | 424/501 |
| 5,821,230 | 10/1998 | Jiang et al. | 514/15 |
| 5,834,520 | 11/1998 | Engel et al. | 514/706 |

FOREIGN PATENT DOCUMENTS

| | | |
|---|---|---|
| 277 829 A2 | 8/1988 | European Pat. Off. . |
| 371 195 A1 | 6/1990 | European Pat. Off. . |
| 611 572 A2 | 8/1994 | European Pat. Off. . |
| 257197 | 6/1988 | Germany . |
| 269 785 A1 | 7/1989 | Germany . |
| 299 265 A5 U | 4/1992 | Germany . |
| 94/11015 | 5/1994 | WIPO . |
| 94/27641 | 12/1994 | WIPO . |

OTHER PUBLICATIONS

Merriam–Webster's Collegiate Dictionary, 10th ed., Merriam–Webster, Incorporated, Springfield, Massachusetts, USA, 1993, p. 263.

Reissman, et al., "Development and Applications of Luteinizing Hormone–Releasing Hormone Antagonists in the Treatment of Infertility: An Overview", Human Reproduction, Bd. 10, Nr. 8, Aug. 1995, pp. 1974–1981.

*Primary Examiner*—F. T. Moezie
*Attorney, Agent, or Firm*—Pillsbury Madison & Sutro LLP

[57] ABSTRACT

In this invention, a release-delaying system is to be developed for LHRH antagonists, in particular for cetrorelix, which allows the active compound to be released in a controlled manner over several weeks by complexation with suitable biophilic carriers.

The acidic polyamino acids polyglutamic acid and polyaspartic acid were selected for complexation with cetrorelix. The cetrorelix polyamino acid complexes are prepared from aqueous solutions by combination of the solutions and precipitation of the complexes, which are subsequently centrifuged off and dried over $P_2O_5$ in vacuo. If complexes having a defined composition are to be obtained, lyophilization proves to be a suitable method. The cetrorelix-carboxylic acid complexes were also prepared from the aqueous solutions.

In the random liberation system, the acidic polyamino acids poly-Glu and poly-Asp showed good release-delaying properties as a function of the hydrophobicity and the molecular mass of the polyamino acid.

In animal experiments, it was possible to confirm the activity of the cetrorelix-polyamino acid complexes as a depot system in principle. It is thus possible by complexation of cetrorelix with polyamino acids to achieve testosterone suppression in male rats over 600 hours. The release of active compound here can be controlled by the nature and the molecular mass of the polymers.

7 Claims, 4 Drawing Sheets

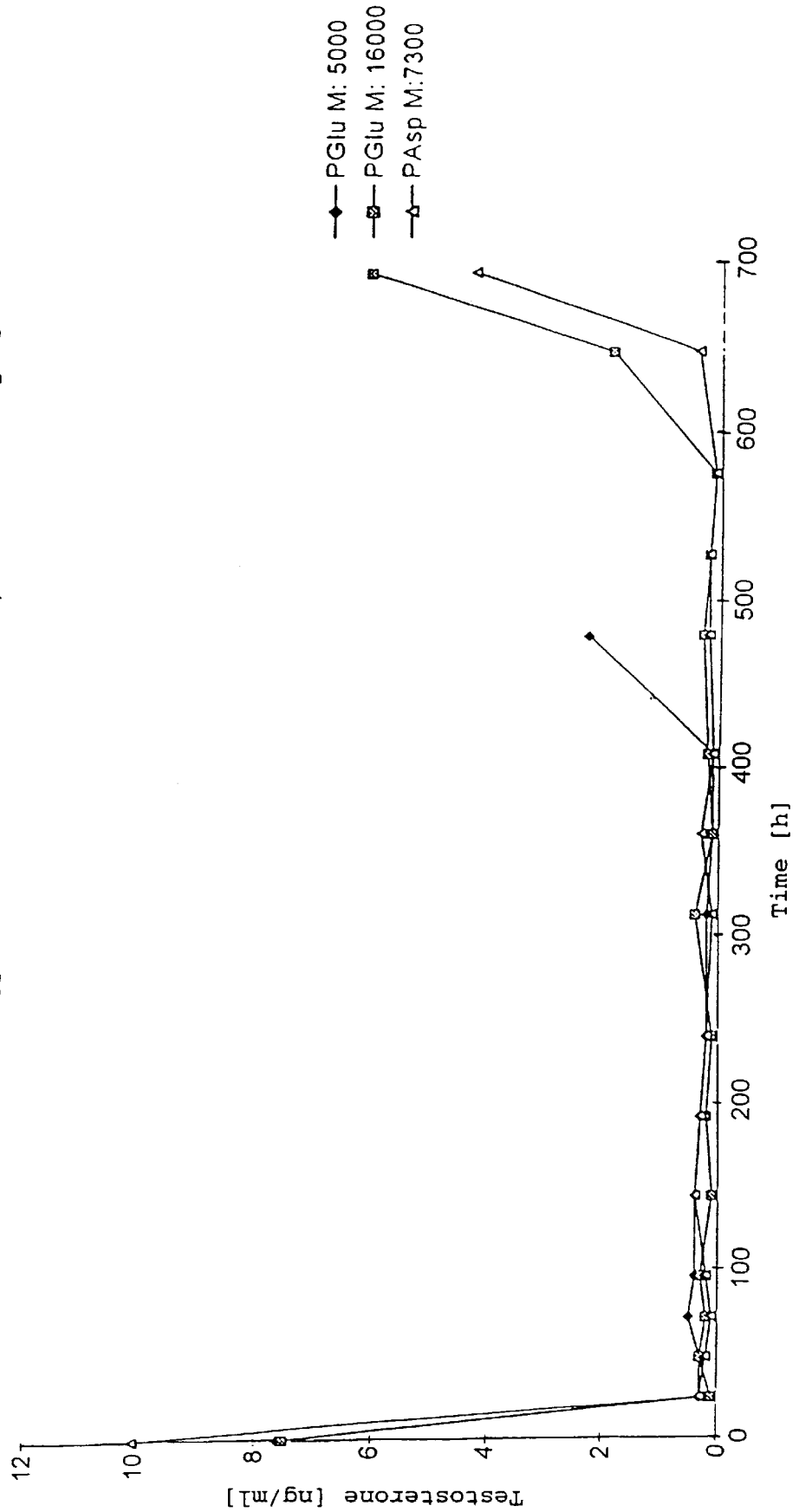

IMMOBILIZED AND ACTIVITY-STABILIZED COMPLEXES OF LHRH ANTAGONISTS AND PROCESSES FOR THEIR PREPARATION

BACKGROUND OF THE INVENTION

The invention relates to activity-stabilized and release-delaying complexes of LHRH antagonists such as antide, antarelix, azaline, A-75998, ganirelix, Nal-Glu antagonist with polyamino acids, in particular polyglutamic acid and polyaspartic acid, and processes for the preparation thereof and pharmaceuticals comprising these.

The peptide hormone-polyamino acid complexes prepared can be used in medicine, for example for the therapy of hormone-sensitive tumours, such as, for example, breast and prostate carcinoma, benign prostate hypertrophy and in gynaecology for the treatment of endometriosis, hysteroscopy and for the treatment of fertility disorders.

BACKGROUND INFORMATION

In the Patent Specifications DD 257197, DD 269785 and DD 299265, for insulin and for other biologically active proteohormones, processes for the preparation of immobilized peptide preparations stabilized in their biological activities and modified in their pharmacological properties are described, whose most important feature is the complexation of the respective peptide with polyamino acids.

In the patents mentioned, preparation procedures are described in which the complexes are formed under the action of formic acid and organic solvents such as chloroform and drastic preparation conditions. There is the danger for the peptide hormone in these processes of partial inactivation and decreased stability.

In the literature, in 1981 for the first time, poorly soluble salts or complexes of LHRH analogues were described in EP 0042753 and EP 0049628. The preparation of these complexes was carried out with a view to the development of pharmaceutical products for different medicinal applications.

In 1989, ORSOLINI in DE Patent 38 22 459 describes the preparation of water-insoluble polypeptides by complexation of LHRH analogues with embonic acid, tannin and stearic acid. The poorly soluble complexes obtained are in this case additionally embedded in a polymeric matrix of (lactic acid-glycolic acid) copolymer.

Further processes for the preparation of Cetrorelix complexes embedded in a (lactic acid-glycolic acid) copolymer were described in 1993 by ORSOLINI and HEIMGARTNER in DE Patents 42 23 282 and 42 23 284. In this patent, poorly soluble Cetrorelix complexes with embonic acid, tannin, stearic acid and palmitic acid [lacuna] mentioned.

SUMMARY OF THE INVENTION

The aim of the invention is to prepare depot preparations having improved and controllable release-delaying properties and increased stability against premature proteolytic degradation of LHRH antagonists for therapy in the areas known for this such as hormone-sensitive tumours, such as, for example, breast and prostate carcinoma, benign prostate hypertrophy, endometriosis, hysteroscopy and for the treatment of fertility disorders and to indicate an easily controllable and environmentally friendly process for the production of these preparations.

The object of the invention is to prepare novel depot preparations having improved and controllable release-delaying properties of LHRH antagonists such as antide, antarelix, azaline, A-75998, ganirelix, Nal-Glu antagonist, but preferably cetrorelix, with biodegradable polymers, and a process for their preparation.

According to the invention, the object is achieved by preparing immobilized and activity-stabilized, parenterally administerable peptide hormone preparations from complexes of LHRH antagonists with polyamino acids, in particular polyglutamic acid and polyaspartic acid by precipitating the polyamino acid-peptide hormone complex from aqueous solutions avoiding organic solvents. Advantageously, the polyamino acid-peptide hormone complexes can furthermore be prepared with a controllable hormone content by lyophilization of the aqueous solutions. By means of the nature and the molecular mass of the polyamino acids, by incorporation of hydrophobic amino acids into the polymer structure or by partial esterification, the release rate of the active compound can be controlled (FIGS. 2 and 3).

The complexes according to the invention are used in medicine for the therapy of hormone-sensitive tumours, in particular for the treatment of breast and prostate carcinomas, of benign prostate hypertrophy and in gynaecology for the induction of ovulation, in vitro fertilization and endometriosis and in connection with hysteroscopy.

The term "complex" in the context of this invention comprises the assembly of two or more components to give a poorly soluble system which is subject to no proven stoichiometry. In this case, a superposition of interactions occurs, mainly secondary valence bonds playing a part.

In the literature, poorly soluble peptide complexes are occasionally also described as a "salt". This description is likewise in many cases not exact, since they are not, as already mentioned, substances having a defined composition.

In peptides and proteins ionic interactions admittedly occur, but they are not responsible on their own for a structural or physical state change.

For peptides and proteins, the term "complex" and "salt" is to be taken in a wider sense on account of the large number of functional groups, since several interactions which lead to synthesis and structure of the peptides and proteins are superimposed.

Polyamine [sic] acids were used which are suitable as biophilic carrier materials for peptides. It is essential to the invention here that the active compounds are not bonded chemically to the polymer, but are only attached to the polymer by secondary valence bonds and hydrophobic interactions.

Unexpectedly, it is seen that the LHRH antagonist Cetrorelix especially has a very high binding affinity to polyamino acids, in particular to polyglutamic acid and polyaspartic acid. Such a high affinity of cetrorelix was not foreseeable on the basis of the literature up to now and was surprising on the basis of the structure of the peptide.

The spontaneously precipitating complexes have a defined, reproducible hormone content.

Should the hormone content in the complexes vary, however, and be defined exactly, lyophilization has turned out as a suitable method.

These preparation conditions are significantly milder than described in earlier patents and thus prevent possible inactivation of the hormone.

The interactions occurring between the molecules on mixing the solutions lead to stable complexes which have a controllable active compound release profile and an increased stability to proteolysis.

Polyamino acids thus affect not only the release-delaying behaviour, but simultaneously offer protection from undesired, premature proteolytic degradation. This aspect is especially of importance in view of the long-term use of such preparations.

The release-delaying behaviour of the complexes can be significantly affected by the nature and the molecular mass of the polyamino acids, the incorporation of amino acids having hydrophobic side chains into the polymer structure and by partial esterification of carboxyl groups present.

BRIEF DESCRIPTION OF THE DRAWINGS

FIG. 4 shows testosterone suppression in male rats after a single s.c. injection of 1.5 mg/kg.

DETAILED DESCRIPTION OF THE INVENTION

The invention is illustrated in greater detail with the aid of the following working examples without, however, restricting it.

Preparation of polyamino acid-peptide complexes by precipitation

EXAMPLE 1

50 mg of polyamino acid are dissolved in 5 ml of $H_2O$, in the case of poly-Glu with addition of 1N $NH_4OH$, gentle warming to 40° C. and ultrasonic treatment. 50 mg of cetrorelix (as the acetate) are dissolved in 4 ml of $H_2O$. The polyamino acid solution is stirred and the cetrorelix solution is added in one step and then stored at 4° C. for 4 h. Afterwards, the precipitate is centrifuged off at 4000 rpm for 5 min, the supernatant is removed and the precipitate is dried over $P_2O_5$ in vacuo for 24 hours. Since no stoichiometric complexes are present, the yield was based on the sum of the starting substances.

Figure 1:
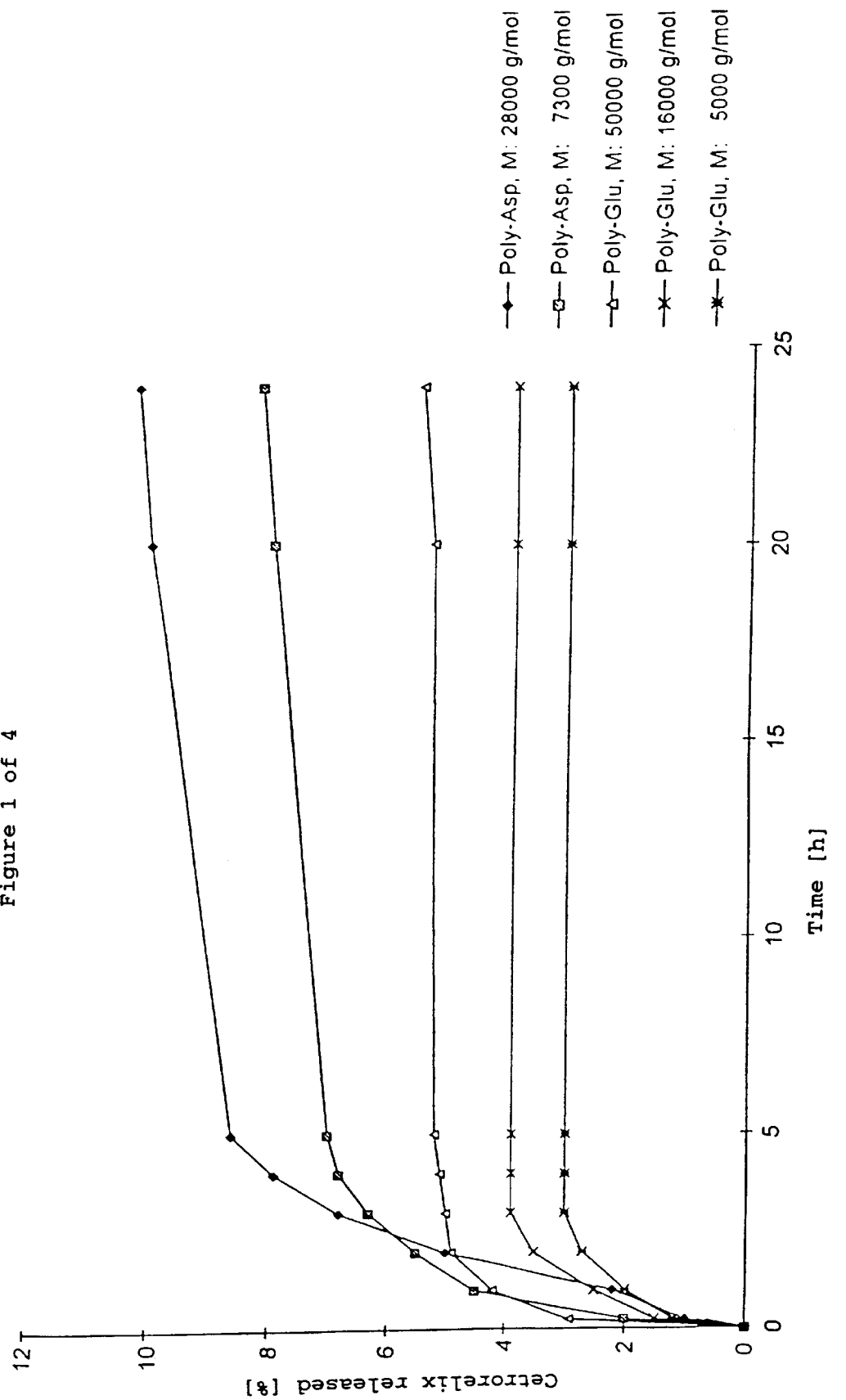
FIG. 1 shows release curves in the random liberation system as a function of molecular mass.

FIG. 1 shows various release curves in the random liberation system as a function of the molecular mass (release medium: 0.01 m ammonium acetate, pH 7.0)

Yield: 50–65% of theory

Cetrorelix content in the complex: see Table 1

TABLE 1

Composition of the precipitated Cetrorelix-polyamino acid complexes

| Polyamino acid | Average molecular mass [g/mol] | Hormone content in the complex [%] rel. error: 5% | Molar ratio Hormone: PAS | Molar ratio Hormone: free carboxyl groups |
|---|---|---|---|---|
| Polyglutamic acid | 5000 | 86 | 1:0.05 | 1:1.9 |
|  | 16000 | 85 | 1:0.016 | 1:2.1 |
|  | 50000 | 60 | 1:0.02 | 1:8.2 |
| Methyl polyglutamate Degree of methylation: |  |  |  |  |
| 2.2% | 16000 | 81 | 1:0.02 | 1:2.8 |
| 24.4% | 16000 | 58 | 1:0.06 | 1:6.7 |
| Polyaspartic acid | 7300 | 86 | 1:0.03 | 1:2.2 |
|  | 14000 | 78 | 1:0.03 | 1:3.8 |
|  | 28000 | 69 | 1:0.023 | 1:6.1 |
| Poly[(Glu,Phe)/4:1] | 45000 | 65 | 1:0.017 | 1:4.5 |
| Poly[(Glu,Leu)/4:1] | 70000 | 79 | 1:0.005 | 1:2.4 |

Preparation of polyamino acid-peptide complexes having a defined peptide content by lyophilization

EXAMPLE 2

Cetrorelix complex having a 50% peptide content 50 mg of polyamino acid are dissolved in 5 ml of $H_2O$, in the case of poly-Glu with addition of 1N $NH_4OH$, gentle warming to 40° C. and ultrasonic treatment. 50 mg of cetrorelix (as the acetate) are dissolved in 4 ml of $H_2O$. The polyamino acid solution is stirred and the cetrorelix solution is added all at once and stirred for a further 2 min. The resulting complex is frozen at −20° C. and subsequently lyophilized. Since no stoichiometric complexes are present, the yield was based on the sum of the starting substances.

Yield: 90–95% of theory Cetrorelix content in the complex: 45–50%

EXAMPLE 3

By appropriate modification of the amount of polyamino acid and cetrorelix, a 70% cetrorelix complex was prepared analogously

EXAMPLE 4

Figure 2:
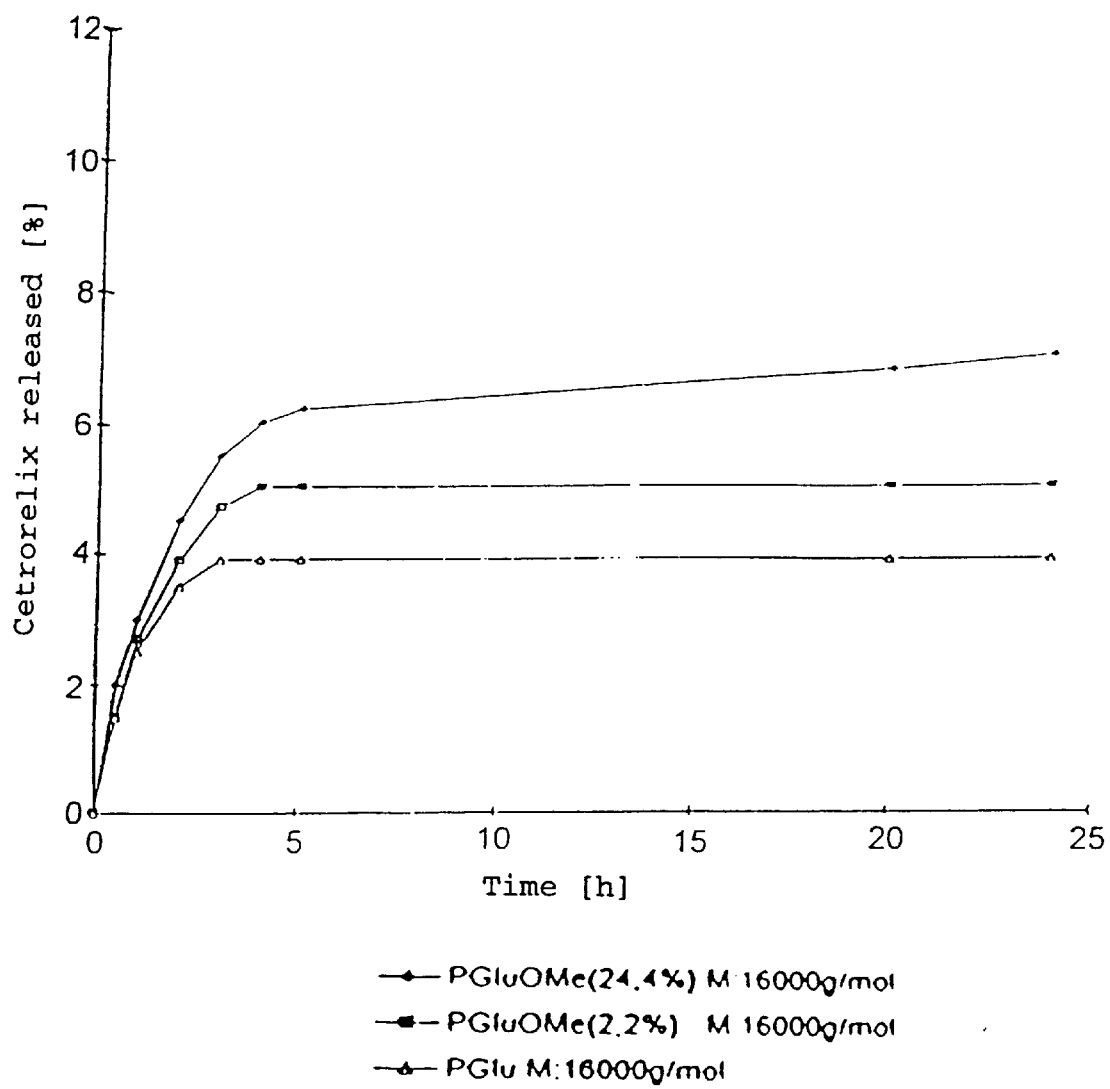
FIG. 2 shows release curves of Cetrorelix complexes with methyl polyglutamate.
Figure 3:
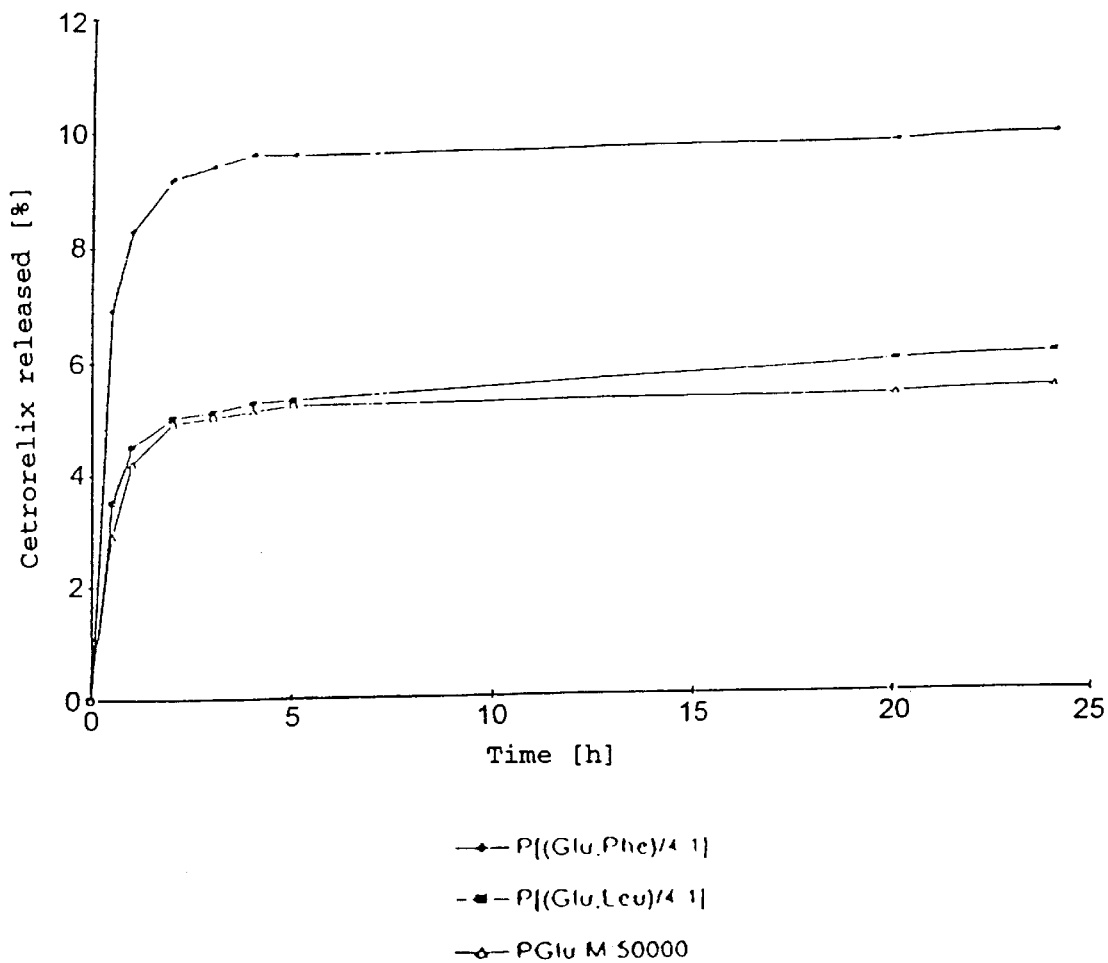
FIG. 3 shows release curves of Cetrorelix complexes with polyglutamic acid with leucine and phenylalanine.

An increase in the hydrophobicity, connected with an increase in the release-delaying behaviour, can be achieved, inter alia, by the partial esterification of carboxyl groups. In FIG. 2, the release curves of Cetrorelix complexes with methyl polyglutamates are shown. FIG. 3 shows the release curves of the Cetrorelix complexes of polyglutamic acid with leucine and phenylalanine.

EXAMPLE 5

For checking of the in vitro release experiments, Cetrorelix-polyamino acid complexes were tested in an animal experiment.

What is concerned here is the Cetrorelix complexes with the following polyamino acids:

Polyglutamic acid, M: 5000 g/mol

Polyglutamic acid, M: 16000 g/mol

Polyaspartic acid, M: 7300 g/mol

In FIG. 4, testosterone suppression in male rats is shown after a single s.c. injection of 1.5 mg/kg. 5 animals were tested per experimental group.

Using these results, it was possible to show that the complexes investigated have a long-term effect in testosterone suppression over 600 hours. (FIG. 4)

The activity and suitability of the cetrorelix-polyamino acid complexes in principle as a depot preparation was confirmed.

What is claimed is:

1. A complex of an LHRH antagonist selected from the group consisting of antide, antarelix, azaline, A-75998, ganirelix, Nal-Glu antagonist and cetrorelix with a polyamino acid selected from the group consisting of polyglutamic acid and polyaspartic acid.

2. The complex of claim 1, wherein the average molecular mass of said polyamino acid is 2000–20000 g/mol.

3. A medicament containing at least one complex of the LHRH antagonist according to claim 1 with polyglutamic acid or polyaspartic acid, and optionally including auxiliaries, bulking agents and/or stabilizers.

4. The medicament according to claim 3, wherein the average molecular mass of polyamino acids is 2000–20000 g/mol.

5. The medicament according to claim 3, wherein the LHRH antagonist is cetrorelix.

6. A method for the treatment of a hormone sensitive tumor, benign prostate hypertrophy, a fertility disorder or endometriosis comprising the administration of a compound according to claim 1.

7. The method of claim 6, said tumor is breast, ovarian or prostate carinoma.

* * * * *